US012594279B2

United States Patent
(12) United States Patent
Lee et al.

(10) Patent No.: US 12,594,279 B2
(45) Date of Patent: Apr. 7, 2026

(54) COMPOSITION FOR PREVENTING OR TREATING TNF-α-RELATED DISEASE, COMPRISING HYDROFLUMETHIAZIDE AS ACTIVE INGREDIENT

(71) Applicants: SK CHEMICALS CO., LTD., Seongnam-si (KR); STANDIGM INC., Seoul (KR)

(72) Inventors: Soo Min Lee, Seongnam-si (KR); Jong-In Kim, Seongnam-si (KR); Nam-Jin Gu, Seongnam-si (KR); Jeong-Hoon Kim, Seongnam-si (KR); Dae Hee Han, Seoul (KR); Hee Jung Koo, Seoul (KR)

(73) Assignees: SK CHEMICALS CO., LTD., Seongnam-si (KR); STANDIGM INC., Seoul (KR)

( * ) Notice: Subject to any disclaimer, the term of this patent is extended or adjusted under 35 U.S.C. 154(b) by 416 days.

(21) Appl. No.: 18/035,627

(22) PCT Filed: Nov. 5, 2021

(86) PCT No.: PCT/KR2021/016045

§ 371 (c)(1),
(2) Date: May 5, 2023

(87) PCT Pub. No.: WO2022/098157

PCT Pub. Date: May 12, 2022

(65) Prior Publication Data

US 2023/0414631 A1 Dec. 28, 2023

(30) Foreign Application Priority Data

Nov. 6, 2020 (KR) ........................ 10-2020-0147591

(51) Int. Cl.
*A61K 31/549* (2006.01)
*A61P 19/02* (2006.01)
*A61P 29/00* (2006.01)

(52) U.S. Cl.
CPC ............ *A61K 31/549* (2013.01); *A61P 19/02* (2018.01); *A61P 29/00* (2018.01)

(58) Field of Classification Search
CPC ... A61K 31/549; A61K 31/5415; A61P 19/02; A61P 29/00; A61P 19/00; A61P 37/00;
(Continued)

(56) References Cited

U.S. PATENT DOCUMENTS

2008/0004285 A1 1/2008 De Jonghe et al.

FOREIGN PATENT DOCUMENTS

JP 2019-529441 A 10/2019
KR 10-2006-0133464 A 12/2006
(Continued)

OTHER PUBLICATIONS

Supuran , Diuretics: From Classical Carbonic Anhydrase Inhibitors to Novel Applications of the Sulfonamides, Current Pharmaceutical Design, 2008, 14, 641-648 (Year: 2008).*
(Continued)

*Primary Examiner* — Taylor V Oh
(74) *Attorney, Agent, or Firm* — Sughrue Mion, PLLC

(57) ABSTRACT

A composition for preventing or treating a TNF-α-related disease is disclosed. The composition includes hydroflumethiazide or a pharmaceutically acceptable salt thereof as an active ingredient. The composition can effectively inhibit the expression or activity of TNF-α and exhibits an excellent treatment effect compared to methotrexate (MTX) or hydroxychloroquine (HCQ), which are rheumatoid arthritis
(Continued)

treatment agents currently on the market, and, thus, can be effectively used for prevention or treatment of a TNF-α-related disease.

8 Claims, 5 Drawing Sheets

(58) Field of Classification Search
CPC . A61P 11/00; A61P 3/10; A23L 33/10; A23V 2200/314; A23V 2200/324; A23V 2200/328; A23V 2002/00
USPC ........................................................ 514/223.2
See application file for complete search history.

(56) References Cited

FOREIGN PATENT DOCUMENTS

| | | | |
|---|---|---|---|
| KR | 10-2014-0023396 | A | 2/2014 |
| WO | 2006/087229 | A1 | 8/2006 |

OTHER PUBLICATIONS

International Search Report for PCT/KR2021/016045 dated, Feb. 18, 2022 (PCT/SA/210).
Zhang et al., "Therapeutic potential of TNFα inhibitors in chronic inflammatory disorders: Past and future", Genes & Diseases, 2021, 8, pp. 38-47.
Sastry, "Inhibition of TNF-α synthesis with thalidomide for prevention of acute exacerbations and altering the natural history of multiple sclerosis", Medical Hypotheses, 1999, 53(1), pp. 76-77.
Lv et al., "Anti-TNF-α therapy for patients with sepsis: a systematic meta-analysis", Int J Clin Pract, Apr. 2014, 68, 4, pp. 520-528. doi: 10.1111/ijcp.12382.
Comarmond et al., "Anti TNF-α in refractory Takayasu's arteritis: Cases series and review of the literature", Autoimmunity Reviews 11, 2012, pp. 678-684.
Houwen et al., "Behcet's Disease, and the Role of TNF-α and TNF-α Blockers", Int. J. Mol. Sci. 2020, 21, 3072; doi:10.3390/ijms21093072.
Mastrandrea et al., "Etanercept Treatment in Children With New-Onset Type 1 Diabetes", Diabetes Care, vol. 32, No. 7, Jul. 2009, pp. 1244-1249.
Tejon et al., "A Spontaneous Mouse Model of Lupus: Physiology and Therapy", Lupus—New Advances and Challenges, 2019, DOI: http://dx.doi.org/10.5772/intechopen.85938.
Cavagna et al., "Infliximab in the treatment of adult Still's disease refractory to conventional therapy", Clinical and Experimental Rheumatology, 2001, 19: pp. 329-332.
Anandacoomarasamy et al., "Advanced refractory polymyositis responding to infliximab", Letters to the Editor, Rheumatology, 2005, 44, pp. 563-564.
Campanilho-Marques et al., "Retrospective analysis of infliximab and adalimumab treatment in a large cohort of juvenile dermatomyositis patients", Arthritis Research & Therapy, 2020, 22:79, 9 pages.
Lamprecht et al., "Effectiveness of TNF-α blockade with infliximab in refractory Wegener's granulomatosis", Rheumatology 2002, 41, pp. 1303-1307.
Mukhopadhyay et al., "Role of TNFα in pulmonary pathophysiology", Respiratory Research 2006, 7:125 doi: 10.1186/1465-9921-7-125, 9 pages.
Morjaria et al., "The role of a soluble TNFα receptor fusion protein (etanercept) in corticosteroid refractory asthma: a double blind, randomised, placebo controlled trial", Thorax, 2008, 63, pp. 584-591, doi:10.1136/thx.2007.086314.
Lai et al., "A Novel TNF-α-Targeting Aptamer for TNF-a-Mediated Acute Lung Injury and Acute Liver Failure", Theranostics 2019, vol. 9, Issue 6, pp. 1741-1751.
Tobin et al., "TNFα Inhibitors in the Treatment of Psoriasis and Psoriatic Arthritis", Biodrugs 2005; 19, 1, pp. 47-57, 1173-8804/05/0001-0047.
Valesini et al., "Biological and clinical effects of anti-TNFα treatment", Autoimmunity Reviews 7, 2007, pp. 35-41.
Spicer, Disease Analysis: Psoriasis, www.datamonitorhealthcare.com, Ref Code: DMKC0211548, Dec. 7, 2021, 97 pages.
Mourabet et al., "Anti-TNF Antibody Therapy for Inflammatory Bowel Disease During Pregnancy: A Clinical Review", Current Drug Targets, 2010, 11, pp. 234-241.
Stevens, Disease Analysis: Crohn's disease, Ref Code: DMKC0216632, Oct. 7, 2021, www.datamonitorhealthcare.com, 78 pages.

* cited by examiner

[Fig. 1]
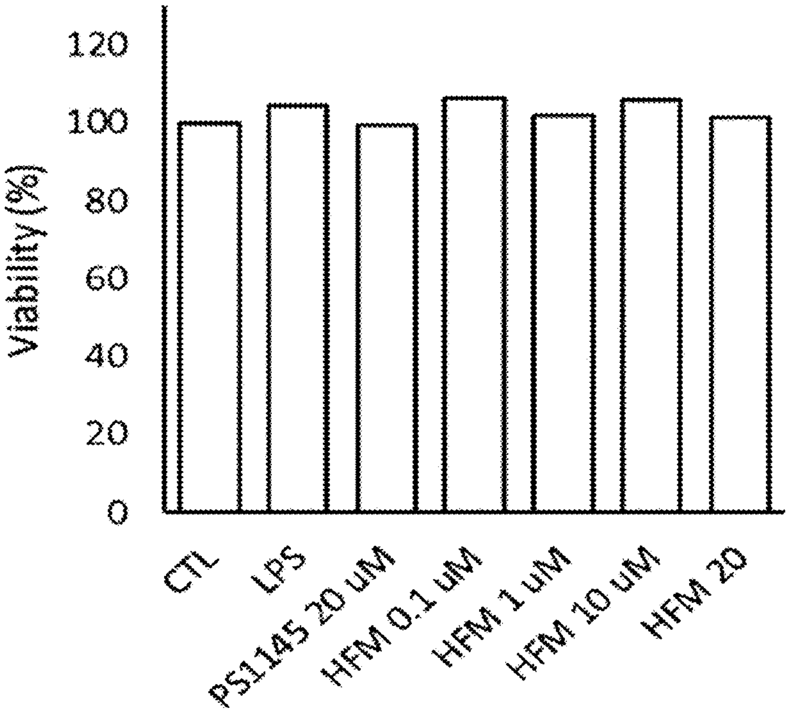
[Fig. 2]
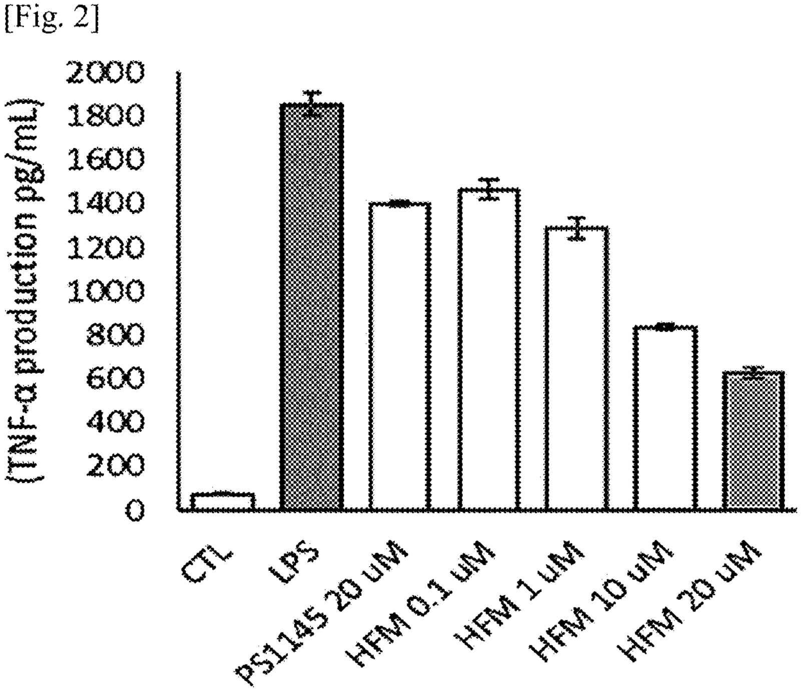

[Fig. 3]
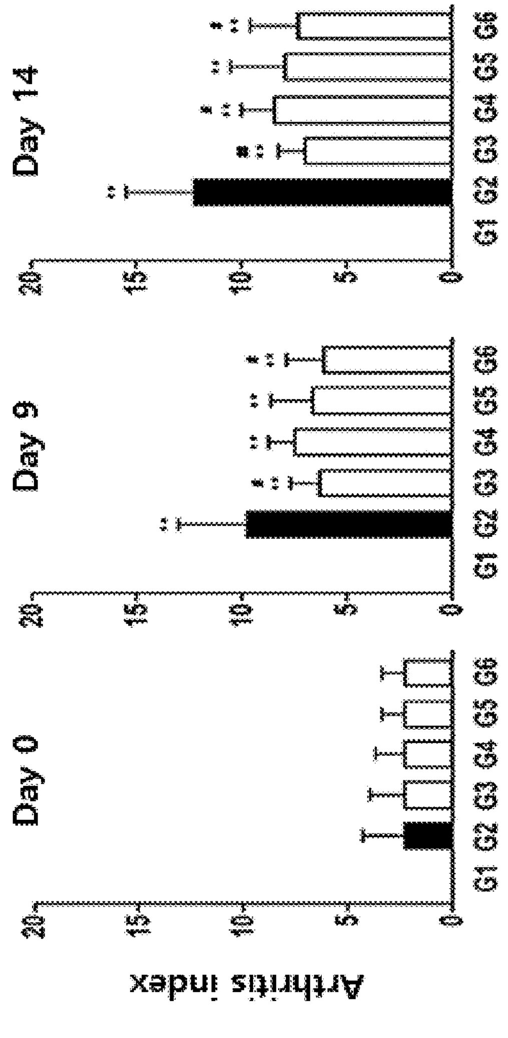

[Fig. 4]
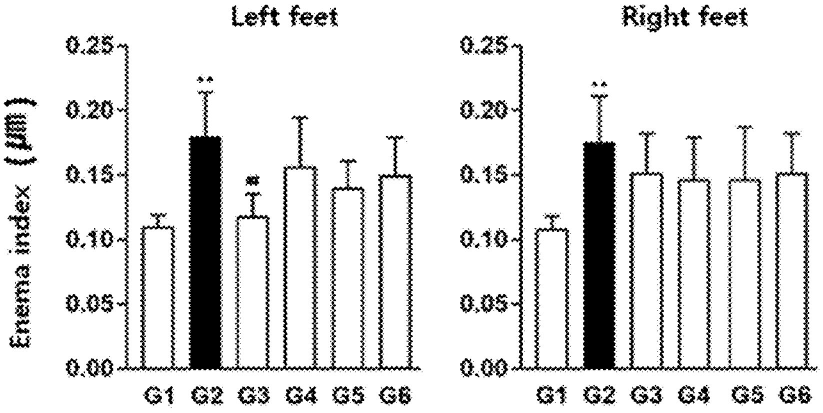

[Fig. 5]
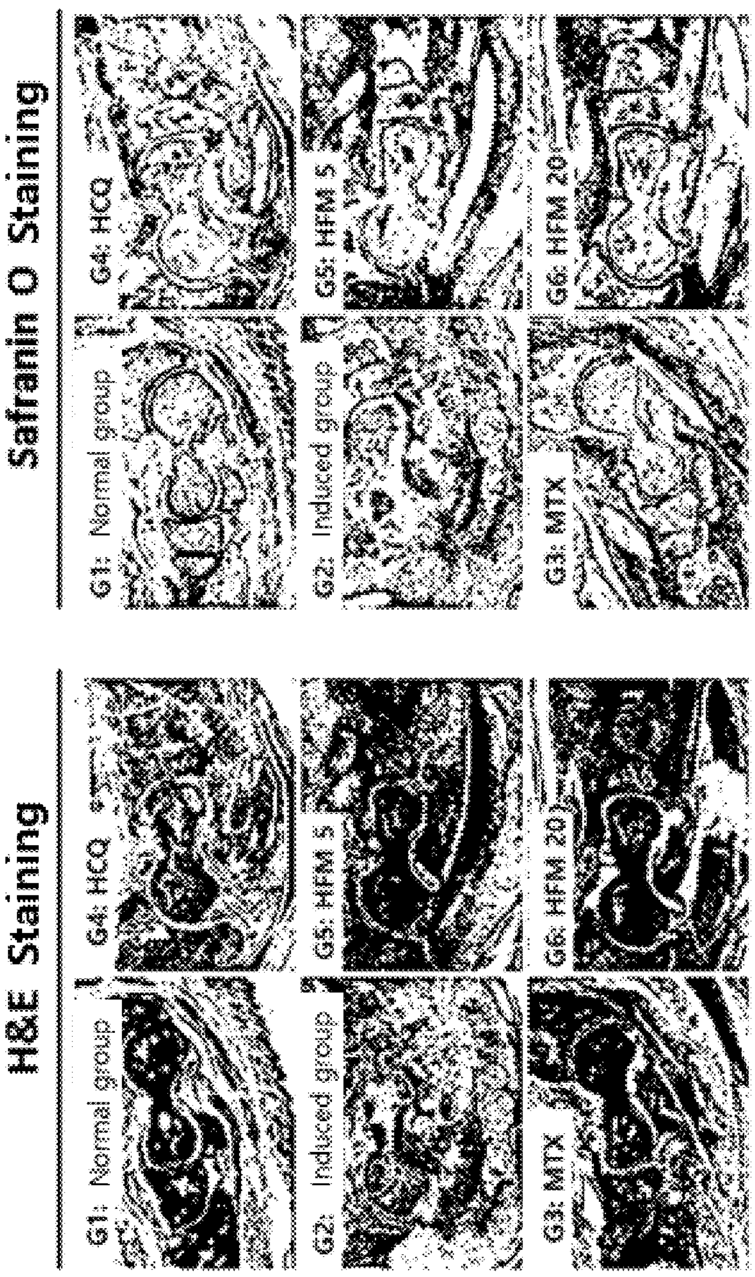

[Fig. 6]
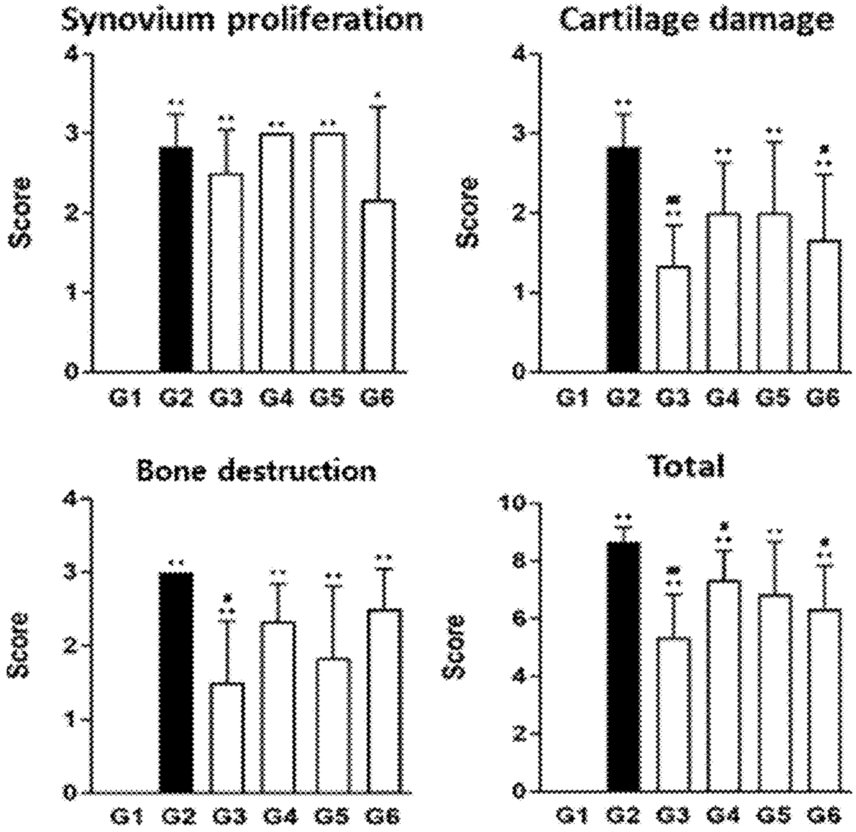

COMPOSITION FOR PREVENTING OR TREATING TNF-α-RELATED DISEASE, COMPRISING HYDROFLUMETHIAZIDE AS ACTIVE INGREDIENT

CROSS REFERENCE TO RELATED APPLICATIONS

This application is a National Stage of International Application No. PCT/KR2021/016045 filed Nov. 5, 2021, claiming priority based on Korean Patent Application No. 10-2020-0147591 filed Nov. 6, 2020.

TECHNICAL FIELD

The present invention relates to a composition for preventing or treating a TNF-α-related disease, including hydroflumethiazide or a pharmaceutically acceptable salt thereof as an active ingredient.

BACKGROUND ART

The inflammatory response, which is one of defense mechanisms of the living body, consists of sophisticated biological signal transduction reactions triggered by infection or wound, and is mediated by various inflammatory cytokines contained therein. In general, a disease that destroys normal tissues as a result of abnormality in such an inflammatory response is called an inflammatory disease, and studies on its detailed mechanism are being actively conducted worldwide.

The inflammation-related signaling pathway is a series of phosphorylation-dephosphorylation chain reactions and may be largely divided into three stages. That is, the inflammation-related signaling pathway consists of: an initial stage of binding an inflammation signal with a biomembrane receptor in a biomembrane to trigger a series of signaling chain reactions; a terminal stage of regulating expression of a gene encoding an inflammation-related protein by means of transcription regulatory factors within a nucleus; and an intermediate stage which consists of a series of signaling chain reactions in a cytoplasm that connect the initial stage with the terminal stage.

Examples of well-known inflammation-causing factors at the initial stage are tumor necrosis factor (TNF; also referred to as TNF-α, a secreted form) and interleukin-1 (IL-1). Examples of well-known representative transcription factors at the terminal stage are activating protein-1 (AP-1), nuclear transcription factor kappa B (NF-kB), and nuclear factor of activated T cells (NEAT). Factors related to the chain reaction at the intermediate stage are not well known.

Among the inflammation-causing factors, TNF-α is the most powerful among inflammatory cytokines and is produced mainly in activated macrophages and T cells. TNF-α stimulates the production of transcription factors such as NF-kB and c-jun/AP-1 and other inflammatory cytokines such as interleukin-1 (IL-1), interleukin-6 (IL-6), and interleukin-8 (IL-8), and plays an important role in normal inflammatory response and acquired and innate immunity.

TNF-α may exist not only in a free form, but also in a membrane-bound form. These two forms of TNF-α induce an inflammatory response of cells very strongly and promote disease conditions in the tissue. TNF-α bound to the cell membrane exhibits cytotoxicity and inflammatory effects through cell-to-cell contact, is released from the cell membrane in a free form by a tumor necrosis factor alpha converting enzyme (TACE) called adamalysin, and exists outside the cell.

When TNF-α is abnormally produced a lot in inflammatory diseases, it activates various cells in the immune system, causing cytotoxic effects, and pathological reactions such as inflammation, tissue destruction, or organ damage.

Primary administration drugs for various TNF-α-related diseases include steroids, anticancer drugs, or immunosuppressants. However, these primary administration drugs have excellent short-term effects, but have adverse effects and are difficult to use for a long period of time. Antibody medicines which inhibit TNF-α are used as secondary administration drugs, and for example, blockbuster biopharmaceuticals such as Etanercept (Enbrel), adalimumab (Humira), or infliximab (Remicade) are used. Since such antibody medicines are expensive and require repeated injections, the repulsion of the patients is great, and the effect is limited because the treatment effect is not generated in about ⅓ of the patients, and the patients who respond to the medicines may also develop tolerance within several years due to the immunogenicity side effects, and there is the disadvantage that it is difficult to store the medicines because low-temperature storage is essential.

Meanwhile, hydroflumethiazide was first synthesized in the late 1950s as a substance having diuretic activity and has been used as an agent for treating and preventing hypertension. However, it is not known what kind of pharmacological effects hydroflumethiazide shows in immune-related diseases.

In this background, the present inventors have made intensive efforts to develop a composition for the prevention or treatment of TNF-α-related diseases, particularly rheumatoid arthritis, and as a result, they have confirmed that the hydroflumethiazide selected through artificial intelligence (AI) deep learning technology inhibits synovium proliferation, bone destruction, and cartilage damage, thereby completing the present invention.

DISCLOSURE OF INVENTION

Technical Problem

An object of the present invention is to provide a pharmaceutical composition for preventing or treating a TNF-α-related disease, the composition including, as an active ingredient, a compound for effectively preventing or treating a TNF-α-related disease by inhibiting the expression or activity of TNF-α, or a pharmaceutically acceptable salt thereof.

Another object of the present invention is to provide a health functional food composition for preventing or ameliorating a TNF-α-related disease, the composition including the compound or a sitologically acceptable salt thereof as an active ingredient.

Still another object of the present invention is to provide a method for inhibiting the expression or activity of TNF-α in vitro, the method including using the compound or a salt thereof, or a reagent composition including the compound as an active ingredient for the method.

Solution to Problem

In order to achieve the above object, the present invention provides a pharmaceutical composition for preventing or treating a TNF-α-related disease, the composition including hydroflumethiazide or a pharmaceutically acceptable salt thereof as an active ingredient.

In addition, the present invention provides a health functional food composition for preventing or ameliorating a TNF-α-related disease, the composition including hydroflumethiazide or a sitologically acceptable salt thereof as an active ingredient.

Further, the present invention provides a method for inhibiting the expression or activity of TNF-α in vitro, the method including using hydroflumethiazide or a salt thereof.

Furthermore, the present invention provides a reagent composition for inhibiting the expression or activity of TNF-α in vitro, the composition including hydroflumethiazide or a salt thereof as an active ingredient.

In addition, the present invention provides a use of a composition for preventing or treating a TNF-α-related disease, the composition including hydroflumethiazide or a pharmaceutically acceptable salt thereof as an active ingredient.

In addition, the present invention provides a use of a composition for producing a medicine for preventing or treating a TNF-α-related disease, the composition including hydroflumethiazide or a pharmaceutically acceptable salt thereof as an active ingredient.

Further, the present invention provides a method for preventing or treating a TNF-α-related disease, the method including administering, to an individual, a composition including hydroflumethiazide or a pharmaceutically acceptable salt thereof as an active ingredient.

Advantageous Effects of Invention

The pharmaceutical composition for preventing or treating a TNF-α-related disease according to the present invention can effectively inhibit the expression or activity of TNF-α, and can exhibit excellent treatment effects as compared to the currently marketed therapeutic agents for rheumatoid arthritis such as methotrexate (MTX) or hydroxychloroquine (HCQ). Thus, the pharmaceutical composition can be effectively used to prevent or treat a TNF-α-related disease.

BRIEF DESCRIPTION OF DRAWINGS

FIG. 1 shows the results of measuring cell viability after treating RAW 264.7 with DMSO (control; CTL), lipopolysaccharide (LPS), PS1145, or various concentrations of hydroflumethiazide.

FIG. 2 shows the results of measuring the expression level of TNF-α in each group in which RAW 264.7, where an inflammatory response had been induced, was treated with PS1145 or various concentrations (0.1 μM, 1 μM, 10 μM, and 20 μM) of hydroflumethiazide.

FIG. 3 shows the results of measuring the arthritis index in each group on day 9 or 14 after treating the rheumatoid arthritis DBA-1J mouse model with the drug (G1: normal control group, G2: comparative control group, G3: MTX-administered group, G4: HCQ-administered group, G5: 5 mg/kg/day hydroflumethiazide-administered group, and G6: 20 mg/kg/day hydroflumethiazide-administered group).

FIG. 4 shows the results of measuring the edema size on the left and right feet in each group after treating the rheumatoid arthritis DBA-1J mouse model with the drug for 14 days (G1: normal control group, G2: comparative control group, G3: MTX-administered group, G4: HCQ-administered group, G5: 5 mg/kg/day hydroflumethiazide-administered group, and G6: 20 mg/kg/day hydroflumethiazide-administered group).

FIG. 5 shows the results of observing histopathological changes in the ankle regions of the mice in each group sacrificed on day 14 after treating the rheumatoid arthritis DBA-1J mouse model with the drug.

FIG. 6 shows the results of quantifying the degrees of synovium proliferation, bone destruction, and cartilage damage in the ankle regions of the mice in each group sacrificed on day 14 after treating the rheumatoid arthritis DBA-1J mouse model with the drug.

BEST MODE FOR CARRYING OUT THE INVENTION

Hereinafter, the present invention will be described in detail.

In an aspect of the present invention, there is provided a pharmaceutical composition for preventing or treating a TNF-α-related disease, the composition including hydroflumethiazide or a pharmaceutically acceptable salt thereof as an active ingredient.

As used herein, the term "hydroflumethiazide" refers to a compound represented by a molecular formula of $C_8H_8F_3N_3O_4S_2$, and has the structure of Formula 1 below:

[Formula 1]

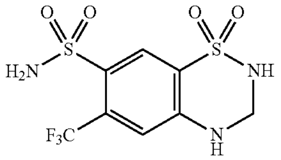

In the present invention, the hydroflumethiazide may inhibit the expression or activity of TNF-α.

In an embodiment of the present invention, macrophages in which the inflammatory response is induced by lipopolysaccharide (LPS) may be treated with hydroflumethiazide to inhibit the expression of TNF-α.

As used herein, the term "TNF-α" refers to tumor necrosis factor-α and is a cytokine which is included in the inflammatory response and a member of an acute-phase protein. TNF-α is mainly secreted by activated macrophages, but is secreted also by various cells such as helper T cells, natural killer cells, and damaged neurons. In addition, the most important role of TNF-α is the regulation of immune cells, and TNF-α, as a heat source in the body, has the ability to induce fever, induce cell suicide, induce sepsis through the production of IL-1 and IL-6, induce cachexia, or induce infection, and inhibit tumor production and viral replication. Abnormal regulation of TNF-α is known to appear in a variety of human diseases such as Alzheimer's disease, cancer, depression, and inflammatory bowel disease (IBD).

In the present invention, the hydroflumethiazide may inhibit synovium proliferation, bone destruction, or cartilage damage.

According to an embodiment of the present invention, hydroflumethiazide is orally administered to an animal model having rheumatoid arthritis induced by TNF-α, thereby exhibiting therapeutic efficacy in a concentration-dependent manner, and exhibiting an anti-arthritic effect that is superior to HCQ, which is a drug on the market, and is similar to MTX.

In the present invention, the TNF-α-related disease may be an autoimmune disease, an inflammatory disease, a respiratory disease, and diabetes. Specifically, the TNF-α-related disease may be at least one selected from the group consisting of rheumatoid arthritis, psoriasis, psoriatic arthritis, ankylosing spondylitis, juvenile idiopathic arthritis, Crohn's disease, ulcerative colitis, multiple sclerosis, sepsis, respiratory diseases, vasculitis, Behcet's disease, type 1 diabetes, systemic lupus erythematosus, adult-onset Still's disease, polymyositis, dermatomyositis, and Wegener's granulomatosis, but is not limited thereto. More specifically, the TNF-α-related disease may be arthritis.

Over-produced TNF-α stimulates macrophages in patients with rheumatoid arthritis to produce proinflammatory mediators that amplify inflammatory reactions. In addition, over-produced TNF-α causes adhesion molecules to be expressed in vascular endothelial cells, thereby enabling them to recruit more inflammatory cells in the inflamed area, and enables fibroblasts to produce proteases, causing damage to cartilage, bone, or ligaments, etc., thereby exacerbating diseases (Jung-Soo Song, Review of Tumor Necrosis Factor Inhibitors on Rheumatoid Arthritis, Journal of Rheumatic Diseases, Vol. 14, No. 1, March 2007). That is, the TNF-α inhibitor is known to be useful for treating or preventing rheumatoid arthritis.

Psoriasis is developed since repeated stimuli such as stress, drugs, or infections in the presence of a genetic predisposition cause the immune system of the skin to activate and affect T cells, and accordingly, cytokines such as TNF-α or IL-17A act to cause epidermal cells to proliferate more than normal (Byeong-cheol Choi, psoriasis and psoriatic arthritis, issue & trend, Korea Pharmaceutical Information Center). That is, the TNF-α inhibitor is known to be useful for treating or preventing psoriasis.

The TNF-α inhibitor is known to be useful for treating patients with psoriatic arthritis since soluble TNF-α receptors, together with TNF-α, in the articular sac of patients with psoriatic arthritis increase more than those of patients with normal arthritis, resulting in tissue damage (Mease P J. Tumour necrosis factor (TNF) in psoriatic arthritis: pathophysiology and treatment with TNF inhibitors. Ann Rheum Dis. 2002 April; 61(4):298-304; and Ritchlin CT1, et al. Group for Research and Assessment of Psoriasis and Psoriatic Arthritis (GRAPPA). Treatment recommendations for psoriatic arthritis. Ann Rheum Dis. 2009 September; 68(9): 1387-94).

Ankylosing spondylitis is a chronic inflammatory disease that appears in the sacroiliac articulation and spine, characterized by new skeletal formation and osteopenia. Since TNF-α plays an important role in the inflammatory response in this disease, the TNF-α inhibitor is used as a therapeutic agent for patients with ankylosing spondylitis (Toussirot E. Biologics in spondyloarthritis: TNFα inhibitors and other agents. Immunotherapy. 2015; 7(6):669-81; and Osman M S, Maksymowych W P. An update on the use of tumor necrosis factor alpha inhibitors in the treatment of ankylosing spondylitis. Expert Rev Clin Immunol. 2017 February; 13(2):125-131).

Juvenile idiopathic arthritis is arthritis that appears in childhood, and the activity of macrophages plays an important role. Since macrophages are major cells that release TNF-α, drugs that inhibit TNF-α are known to be useful for treating patients with juvenile idiopathic arthritis (Mellins E D, et al. Pathogenesis of systemic juvenile idiopathic arthritis: some answers, more questions. Nat Rev Rheumatol 2011; 7(7): 416-26; and Beukelman T, et al. 2011 American College of Rheumatology recommendations for the treatment of juvenile idiopathic arthritis: initiation and safety monitoring of therapeutic agents for the treatment of arthritis and systemic features. Arthritis Care Res (Hoboken). 2011; 63(4):465-482).

Crohn's disease is caused by chronic inflammatory reactions in digestive organs, and since the role of TNF-α is important in these inflammatory reactions, the TNF-α inhibitor has been used as a therapeutic agent for Crohn's disease since 1998 (Adegbola S, et al. Anti-TNF Therapy in Crohn's Disease. Int J Mol Sci. 2018 Jul. 31; 19(8); and Bandzar S, et al. Crohn's disease: a review of treatment options and current research. Cell Immunol. 2013 November-December; 286(1-2):45-52).

Ulcerative colitis is a disease in which the inflamed area usually appears in the colonic mucosa including the rectum, and has a mechanism and symptoms similar to Crohn's disease, so that the TNF-α inhibitor is known to be useful for treating patients with ulcerative colitis (Sands B E, et al. The role of TNFalpha in ulcerative colitis. J Clin Pharmacol. 2007 August; 47(8): 930-41; and Panes J, et al. New treatment strategies for ulcerative colitis. Expert Rev Clin Immunol. 2017 October; 13(10):963-973).

Multiple sclerosis is an autoimmune disease caused by damage to myelin sheath of nerve cells, and TNF-α is known as one of the most important cytokines that cause multiple sclerosis. Therefore, the drug that inhibits TNF-α is known to be useful for treating patients with multiple sclerosis (Sastry P S. Inhibition of TNF-alpha synthesis with thalidomide for prevention of acute exacerbations and altering the natural history of multiple sclerosis. Med Hypotheses. 1999 July; 53(1):76-7).

Sepsis is a systemic inflammatory response caused by infection with microorganisms, and TNF-α is released from monocytes or macrophages, which are major cells of the innate immune response caused by infection. As a result, symptoms such as fever, increased respiratory rate, and increased white blood cells appear, and if the severity worsen, life of the patient may be in danger due to septic shock. Therefore, the drug that inhibits TNF-α is known to be useful for treating or preventing patients with sepsis (Lv S, et al. Anti-TNF-α therapy for patients with sepsis: a systematic meta-analysis. Int J Clin Pract. 2014 April; 68(4):520-8).

In respiratory diseases, since TNF-α causes or exacerbates chronic bronchitis, chronic obstructive pulmonary disease (COPD), asthma, acute lung injury, or acute respiratory distress syndrome (ARDS) which is caused by acute lung injury, the drug that inhibits TNF-α is known to be useful for treating or preventing patients with respiratory diseases (Mukhopadhyay S, et al. Role of TNFalpha in pulmonary pathophysiology. Respir Res. 2006 Oct. 11; 7:125; and Malaviya R, et al. Anti-TNFα Therapy in Inflammatory Lung Diseases bn. Pharmacol Ther. 2017 December; 180: 90-98).

The drug that inhibits TNF-α is known to be useful for treating patients with vasculitis even in the inflammatory response that occurs in vasculitis (Sokumbi 0, et al. Vasculitis associated with tumor necrosis factor-α inhibitors. Mayo Clin Proc. 2012 August; 87(8):739-45; and Jarrot P A, et al. Anti-TNF-alpha therapy and systemic vasculitis. Mediators Inflamm. 2014; 2014:493593).

Behcet's disease is also an autoimmune disease that causes inflammation in blood vessels, mainly showing symptoms such as oral ulcers, genital ulcers, or inflammation in the eyes, and the drug that inhibits TNF-α is known to be useful for treating patients with Behcet's disease (Vallet H, et al. Efficacy of anti-TNF alpha in severe and/or refractory Behηet's disease: Multicenter study of 124 patients. J Autoimmun. 2015 August; 62: 67-74; and Park J, et al. Anti-Tumor Necrosis Factor Therapy in Intestinal Behηet's Disease. Gut Liver. 2018 Nov. 15; 12(6):623-632).

In type 1 diabetes, TNF-α directly destroys beta cells, and thus the drug that inhibits TNF-α is known to be useful for treating patients with type 1 diabetes (CChristen U, et al. A dual role for TNF-alpha in type 1 diabetes: islet-specific expression abrogates the ongoing autoimmune process when induced late but not early during pathogenesis. J Immunol. 2001 Jun. 15; 166(12):7023-32).

Since a high level of TNF-α is detected in plasma even in patients with systemic lupus erythematosus, and a high level of TNF-α is detected even at the onset of nephritis, the drug that inhibits TNF-α is known to be useful for treating or preventing patients with systemic lupus erythematosus (Aringer M, et al. The role of tumor necrosis factor-alpha in systemic lupus erythematosus. Arthritis Res Ther. 2008;

10(1): 202; and Zhu L J, et al. Anti-TNF-alpha therapies in systemic lupus erythematosus. J Biomed Biotechnol. 2010; 2010:465898).

Adult-onset Still's disease is a condition that develops in people in their 30s and which represents a manifestation of Still's disease that typically presents in people under the age of 16, and often occurs in young adults under the age of 35. Since a high level of TNF-α is also detected in plasma and organs in this disease, it is known that the drug that inhibits TNF-α may be useful for treating or preventing patients with adult-onset Still's disease (Al-Homood IA. Biologic treatments for adult-onset Still's disease. Rheumatology (Oxford). 2014 January; 53(1):32-8).

Polymyositis has increased TNF-α level and invasion of macrophages and lymphocytes, which are TNF-α-positive, in the endomysium of the patient. In addition, since there is a correlation between TNF-α levels in the endomysium and myofiber atrophy, it is known that the drug that inhibits TNF-α may be useful for treating or preventing patients with polymyositis (Kalden J R. Emerging role of anti-tumor necrosis factor therapy in rheumatic diseases. Arthritis Res. 2002; 4 Suppl 2:$S_{34}$-40; and Lamprecht P. TNF-alpha inhibitors in systemic vasculitides and connective tissue diseases. Autoimmun Rev. 2005 January; 4(1):28-34).

Since there is a report of a decrease in symptoms when the drug that inhibits TNF-α is used in patients with dermatomyositis, it is expected that the TNF-α inhibitor may be useful for treating or preventing patients with dermatomyositis (Norman R, et al. Case reports of etanercept in inflammatory dermatoses. J Am Acad Dermatol. 2006 March; 54(3 Suppl 2):5139-42).

Patients with Wegener's granulomatosis, a disease characterized by granulomas and vasculitis, typically experience symptoms of the disease in the respiratory organs and kidney. Since there is a report of a decrease in symptoms when patients with Wegener's granulomatosis are treated with the drug that inhibits TNF-α, it is expected that the TNF-α inhibitor may be useful for treating or preventing patients with Wegener's granulomatosis (Lamprecht P, et al. Effectiveness of TNF-alpha blockade with infliximab in refractory Wegener's granulomatosis. Rheumatology (Oxford). 2002 November; 41(11):1303-7).

In the present invention, the pharmaceutically acceptable salt of the hydroflumethiazide may include a salt with an organic acid, an inorganic acid, or an acidic amino acid. Specifically, examples of the salt with an organic acid may include salts derived from acetic acid, propionic acid, isobutyric acid, oxalic acid, maleic acid, malonic acid, succinic acid, glutaric acid, salicylic acid, suberic acid, fumaric acid, mandelic acid, phthalic acid, benzenesulfonic acid, p-tolylsulfonic acid, citric acid, tartaric acid, methanesulfonic acid, an analog thereof, or the like. In addition, examples of the salt with an inorganic acid may include salts derived from hydrochloric acid, hydrobromic acid, nitric acid, carbonic acid, monohydrogencarbonic acid, phosphoric acid, monohydrogenphosphoric acid, dihydrogenphosphoric acid, sulfuric acid, monohydrogensulfuric acid, hydriodic or phosphorous acid, an analog thereof, and the like. In addition, examples of the salt of an acidic amino acid may include salts derived from aspartic acid, glutamic acid, or the like. More specifically, the pharmaceutically acceptable salt of the hydroflumethiazide may be at least one selected from the group consisting of acetic acid, maleic acid, fumaric acid, succinic acid, glutaric acid, and salicylic acid.

In the present invention, the pharmaceutical composition may further include a pharmaceutically acceptable carrier.

The pharmaceutically acceptable carrier included in the pharmaceutical composition of the present invention is commonly used at the time of formulation, and examples thereof may include lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propylhydroxybenzoate, talc, magnesium stearate, mineral oil, saline, phosphate buffered saline (PBS) or a medium, and the like, but is not limited thereto, and may further include a lubricant, a wetting agent, a sweetening agent, a flavoring agent, an emulsifier, a suspending agent, a preservative, and the like, in addition to the above ingredients.

The pharmaceutical composition of the present invention may be prepared in a unit dose form by formulation using a pharmaceutically acceptable carrier and/or excipient or may be prepared by incorporating into a large-capacity container, according to a method which can easily be performed by those skilled in the art to which the present invention belongs, and may further include a dispersant or a stabilizer.

Formulations of the pharmaceutical composition may vary depending on the method of use, but may be prepared as plasters, granules, powders, syrups, solutions, fluidextracts, emulsions, suspensions, infusions, tablets, injections, capsules, pills, and the like. In addition, formulations of the pharmaceutical composition may include ointments, pastes, creams, lotions, gels, powders, solutions, sprays, inhalants, or patches, which are formulations for the topical or transdermal administration.

The pharmaceutical composition may be mixed under sterile conditions with a pharmaceutically acceptable carrier, and with any preservatives, buffers, and the like, if necessary. The formulations of ointments, pastes, creams, and gels according to the present invention may further contain excipients, such as animal and vegetable fats, oils, waxes, paraffins, starch, tragacanth, cellulose derivatives, polyethylene glycols, silicones, bentonites, silicic acid, talc, and zinc oxide, or mixtures thereof.

As used herein, the term "preventing" or "prevention" refers to all acts of delaying the progress of or inhibiting a TNF-α-related disease by administering the composition according to the present invention, and the term "treating" or "treatment" refers to all acts of improving or beneficially changing symptoms of a TNF-α-related disease by administering the composition of the present invention.

The hydroflumethiazide or pharmaceutical composition of the present invention may be administered to a patient in a therapeutically effective amount or a pharmaceutically effective amount.

Here, the "therapeutically effective amount" or "pharmaceutically effective amount" refers to an amount of a compound or composition effective to prevent or treat a target disease, the amount being sufficient to treat the disease at a reasonable benefit/risk ratio, which is applicable to medical treatment, without causing adverse effects. In addition, the "effective amount" refers to an amount sufficient to inhibit or reduce the activity of TNF-α in a TNF-α-related disease either in vitro or in vivo. A level of the effective amount may be determined depending on factors, including the patient's health status, disease type, disease severity, drug activity, drug sensitivity, method of administration, time of administration, route of administration and rate of excretion, duration of treatment, and drugs used simultaneously or in combination, and other factors well known in the medical field.

The hydroflumethiazide or pharmaceutically acceptable salt thereof of the present invention by any suitable route in the form of a pharmaceutical composition adapted to such a route, and in a dose effective for the treatment intended.

The hydroflumethiazide or pharmaceutical composition of the present invention may be administered as an individual therapeutic agent or administered in combination with other therapeutic agents, may be administered sequentially or simultaneously with a conventional therapeutic agent, and may be administered once or multiple times. It is important to take into account all of the above factors and to administer the amount in which the maximum effect can be obtained in a minimal amount without side effects, and such amount may be easily determined by a person skilled in the art.

Specifically, an effective dosage of the hydroflumethiazide of the compound or the pharmaceutically acceptable salt thereof in the composition of the present invention may vary depending on the age, sex, and body weight of the patient, and is typically in the range of about 12.5 mg/kg/day to about 200 mg/kg/day in single or divided doses, and the case of 100 mg or more should be administered in two or more divided doses per day. However, the effective dosage may increase or decrease depending on the route of administration, disease severity, the patient's sex, body weight, age, and the like. Thus, the scope of the present invention is not limited thereto.

For treating a TNF-α-related disease, the hydroflumethiazide or pharmaceutically acceptable salts thereof described herein may be administered in various ways as follows.

The pharmaceutical composition of the present invention may be administered orally, including by swallowing. Through the oral administration, the pharmaceutical composition of the present invention may enter the gastrointestinal tract, or be absorbed directly into the blood stream from the mouth (e.g., buccal or sublingual administration).

Suitable compositions for oral administration may be in the form of solid, liquid, gel, or powder, and may have formulations such as tablets, lozenges, capsules, granules, and powders.

The compositions for oral administration may optionally be enteric coated, and may exhibit delayed or sustained release through the enteric coating. That is, the composition for oral administration according to the present invention may be a formulation having an immediate or modified release pattern.

A liquid formulation may include a solution, a syrup, and a suspension, and the liquid composition may be contained in a soft or hard capsule. Such a formulation may include a pharmaceutically acceptable carrier such as water, ethanol, polyethylene glycol, cellulose, or oil. The formulation may also include one or more emulsifiers and/or suspensions.

In a tablet formulation, the amount of drug, an active ingredient, may be present from about 0.05% to about 95% by weight, more typically from about 2% to about 70% by weight of the formulation, with respect to the total weight of the tablet. In addition, the tablet may contain a disintegrant, comprising from about 0.5% to about 35% by weight, more typically from about 2% to about 25% by weight of the formulation. As examples of the disintegrant, lactose, starch, sodium starch glycolate, crospovidone, croscarmellose sodium, maltodextrin, or a mixture thereof may be used, but the present invention is not limited thereto.

Suitable lubricants included for preparation in a tablet may be present in an amount from about 0.1% to about 10% by weight, and talc, silicon dioxide, stearic acid, calcium, zinc or magnesium stearate, sodium stearyl fumarate, or the like may be used as a lubricant, but the present invention is not limited to the types of such additives.

As a binder for preparation in a tablet, gelatin, polyethylene glycol, sugar, gum, starch, polyvinylpyrrolidone, hydroxypropylcellulose, hydroxypropylmethylcellulose, and the like may be used, and as a suitable diluent for preparation in a tablet, mannitol, xylitol, lactose, dextrose, sucrose, sorbitol, starch, microcrystalline cellulose, and the like may be used, but the present invention is not limited to the types of such additives. The binder may be used in an amount of about 0.1% to about 20% by weight with respect to the total weight of the tablet, and the diluent may be used in an amount of about 0.1% to about 20% by weight with respect to the total weight of the tablet.

A solubilizer that may be optionally included in the tablet may be used in an amount of about 0.1% to about 3% by weight with respect to the total weight of the tablet, and for example, polysorbate, sodium lauryl sulfate, sodium dodecyl sulfate, propylene carbonate, diethylene glycol monoethyl ether, dimethyl isosorbide, polyethylene glycol (natural or hydrogenated) castor oil, HCOR™ (Nikkol), oleyl ester, Gelucire™, caprylic/caprylic acid mono/diglyceride, sorbitan fatty acid esters, and Solutol HS™, and the like may be used in the pharmaceutical composition according to the present invention, but the present invention is not limited to specific types of such solubilizers.

The pharmaceutical composition of the present invention may be directly administered into bloodstream, muscle, or internal organs. Suitable methods for parenteral administration include intravenous, intra-muscular, subcutaneous intraarterial, intraperitoneal, intravertebral, intracranial injections, and the like. Suitable devices for parenteral administration include injectors (including needle and needle-free injectors) and infusion methods.

Compositions for parenteral administration may be in a formulation with an immediate or a modified release pattern, and the modified release pattern may be a delayed or sustained release pattern.

Most parenteral formulations are liquid compositions, and such liquid compositions are aqueous solutions containing an active ingredient, a salt, a buffer, an isotonic agent, and the like according to the present invention.

Parenteral formulations may also be prepared in a dehydrated form (e.g., by lyophilization) or as sterile non-aqueous solutions. These formulations can be used with a suitable vehicle, such as sterile water. Solubility-enhancing agents may also be used in preparation of parenteral solutions.

The pharmaceutical composition of the present invention may be administered topically to the skin or transdermally. Formulations for this topical administration includes lotions, solutions, creams, gels, hydrogels, ointments, foams, implants, patches, and the like. Pharmaceutically acceptable carriers for topical administration formulations may include water, alcohol, mineral oil, glycerin, polyethylene glycol, and the like. Topical administration may also be performed by electroporation, iontophoresis, phonophoresis, and the like.

Compositions for topical administration may be in a formulation with an immediate or a modified release pattern, and the modified release pattern may be a delayed or sustained release pattern.

In another aspect of the present invention, there is provided a health functional food composition for preventing or ameliorating a TNF-α-related disease, the composition including hydroflumethiazide or a sitologically acceptable salt thereof as an active ingredient.

As used herein, the term "food" refers to a natural product or a processed product containing one or more nutrients, preferably, a product which underwent a certain processing process and can be directly eaten, and includes all of foods, food additives, health functional foods, beverages, beverage additives, and the like as a typical meaning.

When the composition of the present invention is prepared as a food composition, the composition may include ingredients commonly added during food production, for example, proteins, carbohydrates, fats, nutrients, seasoning agents, and flavoring agents.

In further another aspect of the invention, there is provided a method for inhibiting the expression or activity of TNF-α in vitro, the method including using hydroflumethiazide or a salt thereof.

In still another aspect of the present invention, there is provided a reagent composition for inhibiting the expression or activity of TNF-α in vitro, the composition including hydroflumethiazide or a salt thereof as an active ingredient.

In yet another aspect of the present invention, there is provided a use of a composition for preventing or treating a TNF-α-related disease, the composition including hydroflumethiazide or a pharmaceutically acceptable salt thereof as an active ingredient.

In still yet another aspect of the present invention, there is provided a use of a composition for producing a medicine for preventing or treating a TNF-α-related disease, the composition including hydroflumethiazide or a pharmaceutically acceptable salt thereof as an active ingredient.

In another aspect of the present invention, there is provided a method for preventing or treating a TNF-α-related disease, the method including administering, to an individual, a composition including hydroflumethiazide or a pharmaceutically acceptable salt thereof as an active ingredient.

In this case, the hydroflumethiazide or pharmaceutically acceptable salt thereof is the same as described above in the pharmaceutical composition.

Mode for Carrying Out the Invention

Hereinafter, the present invention will be described in more detail by way of the following examples.

However, the following examples are only for illustrating the present invention, and the scope of the present invention is not limited thereto.

Example 1. Effect of Inhibiting TNF-α Expression of Hydroflumethiazide in Induced Inflammatory Cells The present inventors have selected hydroflumethiazide as a substance expected to have a therapeutic effect on a TNF-α-related disease, particularly, rheumatoid arthritis, through a screening method using artificial intelligence deep learning technology.

Macrophages (RAW 264.7; TIB-71) were purchased from ATCC, and treated with DMSO, lipopolysaccharide (LPS), PS1145, or various concentrations of hydroflumethiazide as shown in Table 1 below, and then it was confirmed through MTT assay that cytotoxicity was not exhibited (FIG. 1).

The "PS1145" means N-(6-chloro-9H-pyrido[3,4-b]indol-8-yl)-3-pyridinecarboxamide dihydrochloride, is known as an IkB kinase (IKK) inhibitor, and has the structure of Formula 2 below:

[Formula 2]

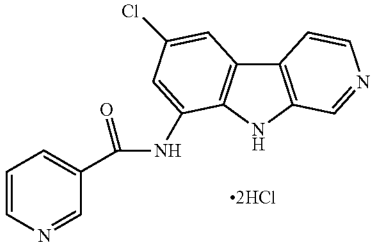

TABLE 1

| Drug | Treatment concentration (uM) | Viability (%) | TNF-α (pg/mL) | Inhibition (%) |
|---|---|---|---|---|
| DMSO | 0.01% (v/v) | 100.00 | 75.67 | |
| LPS | 10 ng/ml | 104.31 | 1852.38 | |
| PS1145 | 20 | 99.16 | 1402.08 | 24.31 |
| Hydroflumethiazide | 0.1 | 106.35 | 1466.48 | 20.83 |
| (HFM) | 1 | 101.82 | 1289.62 | 30.38 |
| | 10 | 105.73 | 837.44 | 54.79 |
| | 20 | 101.11 | 625.65 | 66.22 |

In addition, in order to confirm an effect of inhibiting the TNF-α expression of hydroflumethiazide in induced inflammatory cells, an experiment was performed as follows. RAW 264.7 cells were treated with DMSO at a concentration of 0.01% (v/v) as an untreated control group, and the cells were treated with LPS at a concentration of 10 ng/ml as a control group to induce an inflammatory response. In addition, as shown in Table 1, RAW 264.7 cells, in which the inflammatory response was induced by treating LPS as an experimental group, were treated with PS1145 or various concentrations (0.1 μM, 1 μM, 10 μM, and 20 μM) of hydroflumethiazide. Then, the expression level of TNF-α was measured and compared through the ELISA method in the groups treated with respective drugs.

As a result, when the inflammatory response-induced RAW 264.7 cells were treated with at least 0.1 μM of hydroflumethiazide, the expression level of TNF-α was decreased by at least 20%, and in the group treated with at least 1 μM of hydroflumethiazide, the expression level of TNF-α was further decreased compared to the group treated with PS1145 (FIG. 2). In particular, the groups in which the inflammatory response-induced RAW 264.7 cells were treated with at least 10 μM of hydroflumethiazide showed a significant decrease in the expression of TNF-α by at least 50%.

Accordingly, it was confirmed that hydroflumethiazide has the effect of inhibiting the expression of TNF-α in inflammatory cells.

Example 2. Effect of Treating Arthritis of Hydroflumethiazide Using Animal Model

Example 2.1. Experimental Method

DBA-1J mice were purchased from Central Lab. Animal Inc. Bovine Type II collagen (2 mg/mL) was emulsified in 4 mg/mL of Complete Freund's adjuvant at 1:1, and then injected subcutaneously to the DBA-1J mice at the base of the tail with 100 μL/head to induce arthritis first. Then, after 3 weeks, Bovine Type II collagen (2 mg/mL) was emulsified in Incomplete Freund's adjuvant at 1:1 and injected subcutaneously to the DBA-1J mice at the base of the tail with 100 μL/head to prepare rheumatoid arthritis animal models.

As a normal control group, 0.5% methyl cellulose (MC) was orally administered to healthy DBA-1J mice, and as a comparative control group, 0.5% MC was orally administered to the prepared rheumatoid arthritis mouse models, daily for 2 weeks. Methotrexate (MTX, 2 mg/kg/2 day), hydroxychloroquine (HCQ, 80 mg/kg/day), which are commercially available therapeutic agents for rheumatoid arthritis, and hydroflumethiazide (5 mg/kg/day or 20 mg/kg/day) were orally administered daily for 2 weeks to the prepared rheumatoid arthritis mouse models, respectively. The composition of each experimental group is shown in Table 2 below.

TABLE 2

| Group | Sex | Number of animals (head) | Arthritis induced | Administered substance | Method of administration | Amount of administration |
|---|---|---|---|---|---|---|
| G1 | M | 6 | N | 0.5% MC | Oral | — |
| G2 | M | 6 | Y | 0.5% MC | Oral | — |
| G3 | M | 6 | Y | MTX | Oral | 2 (2 d) |
| G4 | M | 6 | Y | HCQ | Oral | 80 |
| G5 | M | 6 | Y | HFM | Oral | 5 |
| G6 | M | 6 | Y | HFM | Oral | 20 |

Example 2.2. Measurement of Arthritis Index and Size of Lower Extremity Edema Arthritis indices were measured on day 9 and 14 after the administration of each drug in each of the control groups and experimental groups on the basis of the following criteria. Reference: 0, No edema or swelling: 1, Mild edema and redness confined to the joint: 2, Mild edema and redness from the joint to carpal bone and tarsal bone: 3, Moderate edema and redness from the joint to carpal bone and tarsal bone: 4, Overall edema and redness and joint stiffness: 5. In the arthritis index, the highest score was set to 16 points by summing up the four limb scores. In addition, the size of the lower extremity edema was measured using a micrometer on day 14 after each drug was administered in each of the control groups and experimental groups.

The arthritis index of each group is shown in Table 3 below, and the size of the lower extremity edema is shown in Table 4 below (N=the number of animals (head), **/* A significant difference at $p<0.01/p<0.05$ level compared to the G1, ##/#A significant difference at $p<0.01/p<0.05$ level compared to the G2).

As a result, the arthritis index was significantly decreased from day 9 of the administration in the hydroflumethiazide-administered group compared to the HCQ-administered group, and the arthritis index and the size of the lower extremity edema in the group administered with a high concentration (20 mg/kg/day) of hydroflumethiazide were decreased at a similar level to the MTX-administered group on day 14 (FIGS. 3 and 4).

Thus, it was confirmed that the oral administration of hydroflumethiazide has a therapeutic effect in the rheumatoid arthritis animal models.

Example 2.3. Histopathological Observation

On day 14 of administration, the mice in each of the control groups and experimental groups were sacrificed, and then joint staining photographs were taken through the following process. The ankle areas of the sacrificed mice were subjected to general tissue treatment processes such as demineralization, trimming, dehydration, paraffin embedding, and microtome cutting to prepare specimens for histopathological examination. Then, Hematoxylin & Eosin

TABLE 3

| | Groups | | | | | |
|---|---|---|---|---|---|---|
| Day | G1: Normal group | G2: Arthritis induced group | G3: MTX | G4: HCQ | G5: HFM 5 | G6: HFM 20 |
| 0 | 0 ± 0 | 2.3 ± 2 | 2.3 ± 1.6 | 2.3 ± 1.4 | 2.3 ± 1 | 2.3 ± 1 |
| 2 | 0 ± 0 | $4.7 \pm 2.3^{**}$ | $4.2 \pm 1.0^{**}$ | $4.7 \pm 1.2^{**}$ | $4.2 \pm 1.6^{**}$ | $4 \pm 1.7^{**}$ |
| 4 | 0 ± 0 | $5.7 \pm 2.7^{**}$ | $5 \pm 1.3^{**}$ | $6 \pm 1.3^{**}$ | $5.8 \pm 1.8^{**}$ | $5 \pm 1.4^{**}$ |
| 7 | 0 ± 0 | $9.2 \pm 3.5^{**}$ | $5.8 \pm 1.3^{**}$ | $7 \pm 1.3^{**}$ | $6 \pm 2.1^{**}$ | $5.7 \pm 1.5^{**}$ |
| 9 | 0 ± 0 | $9.8 \pm 3.2^{**}$ | $6.3 \pm 1.4^{**,\#}$ | $7.5 \pm 1.2^{**}$ | $6.7 \pm 2.0^{**}$ | $6.2 \pm 1.7^{**,\#}$ |
| 11 | 0 ± 0 | $11 \pm 3.9^{**}$ | $6.7 \pm 1.5^{**}$ | $7.8 \pm 1.2^{**}$ | $7.2 \pm 1.7^{**}$ | $6.8 \pm 1.6^{**}$ |
| 14 | 0 ± 0 | $12.3 \pm 3.1^{**}$ | $7 \pm 1.3^{**,\#\#}$ | $8.5 \pm 1.5^{**,\#}$ | $8 \pm 2.5^{**}$ | $7.3 \pm 2.3^{**,\#}$ |
| N | 6 | 6 | 6 | 6 | 6 | 6 |

TABLE 4

| Day | G1: Normal group | G2: Induced group | G3: MTX | G4: HCQ | G5: HFM 5 | G6: HFM 20 |
|---|---|---|---|---|---|---|
| | | | Left Feet | | | |
| 0 | 0.1 ± 0.01 | 0.11 ± 0.03 | 0.11 ± 0.02 | 0.12 ± 0.02 | 0.09 ± 0.01 | 0.11 ± 0.03 |
| 14 | 0.11 ± 0.01 | $0.18 \pm 0.03^{**}$ | $0.12 \pm 0.02^{\#\#}$ | 0.16 ± 0.04 | 0.14 ± 0.02 | 0.15 ± 0.03 |
| | | | Right Feet | | | |
| 0 | 0.1 ± 0.01 | 0.11 ± 0.03 | 0.1 ± 0.02 | 0.11 ± 0.02 | 0.11 ± 0.03 | 0.1 ± 0.01 |
| 14 | 0.11 ± 0.01 | $0.18 \pm 0.04^{**}$ | 0.15 ± 0.03 | 0.15 ± 0.03 | 0.15 ± 0.04 | 0.15 ± 0.03 |
| N | 6 | 6 | 6 | 6 | 6 | 6 |

(H&E) and safranin-O stainings were performed, and histopathological changes were observed using an optical microscope (FIG. 5).

In addition, the degrees of synovium proliferation, bone destruction, and cartilage damage were quantified, and the results are shown in Table 5 below.

TABLE 5

| Tests | Groups | | | | | |
|---|---|---|---|---|---|---|
| | G1: Normal group | G2: Induced group | G3: MTX | G4: HCQ | G5: HFM 5 | G6: HFM 20 |
| Synovium proliferation | 0 ± 0 | 2.8 ± 0.4** | 2.5 ± 0.5** | 3 ± 0.0** | 3 ± 0.0** | 2.2 ± 1.2* |
| Cartilage damage | 0 ± 0 | 2.8 ± 0.4** | 1.3 ± 0.5**,## | 2 ± 0.6** | 2 ± 0.9** | 1.7 ± 0.8**,# |
| Bone destruction | 0 ± 0 | 3 ± 0.0** | 1.5 ± 0.8**,# | 2.3 ± 0.5** | 1.8 ± 1.0** | 2.5 ± 0.5** |
| Total | 0 ± 0 | 8.7 ± 0.5** | 5.3 ± 1.5**,## | 7.3 ± 1.0**,# | 6.8 ± 1.8** | 6.3 ± 1.5**,# |
| N | 6 | 6 | 6 | 6 | 6 | 6 |

Thus, it was confirmed that hydroflumethiazide showed a therapeutic efficacy on rheumatoid arthritis already induced by TNF-α in a concentration-dependent manner, and exhibited an anti-arthritic effect superior to HCQ, which is a drug on the market, and an anti-arthritic effect similar to MTX (FIG. 6).

The invention claimed is:

1. A method for treating a tumor necrosis factor-α (TNF-α)-related disease in a subject in need thereof, the method comprising administering, to the subject, an effective amount of a composition comprising hydroflumethiazide or a pharmaceutically acceptable salt thereof as an active ingredient, wherein the TNF-α-related disease is synovium proliferation, bone destruction, cartilage damage, arthritis, psoriasis, ankylosing spondylitis, Crohn's disease, ulcerative colitis, multiple sclerosis, sepsis, a respiratory disease, vasculitis, Behcet's disease, type 1 diabetes, systemic lupus erythematosus, adult-onset Still's disease, polymyositis, dermatomyositis, Wegener's granulomatosis, or a combination thereof, and wherein the treatment of the TNF-α-related disease is delaying progress of the TNF-α-related disease, or improving or beneficially changing symptoms of the TNF-α-related disease.

2. The method of claim 1, wherein the arthritis is rheumatoid arthritis, psoriatic arthritis, or juvenile idiopathic arthritis.

3. The method of claim 1, wherein the composition is a food or a dietary supplement.

4. A method of inhibiting expression or activity of tumor necrosis factor-α (TNF-α) in a subject in need thereof, the method comprising administering to the subject an effective amount of a composition comprising hydroflumethiazide or a pharmaceutically acceptable salt thereof as an active ingredient.

5. The method of claim 4, wherein the subject suffers from synovium proliferation, bone destruction, or cartilage damage.

6. The method of claim 4, wherein the subject suffers from synovium proliferation, bone destruction, cartilage damage, arthritis, psoriasis, ankylosing spondylitis, Crohn's disease, ulcerative colitis, multiple sclerosis, sepsis, a respiratory disease, vasculitis, Behcet's disease, type 1 diabetes, systemic lupus erythematosus, adult-onset Still's disease, polymyositis, dermatomyositis, Wegener's granulomatosis, or a combination thereof.

7. The method of claim 4, wherein the arthritis is rheumatoid arthritis, psoriatic arthritis, or juvenile idiopathic arthritis.

8. The method of claim 4, wherein the composition is a food or a dietary supplement.

* * * * *